United States Patent [19]

Rudolph et al.

[11] 4,442,676
[45] Apr. 17, 1984

[54] PROCESS FOR IMPROVING THE THERMAL STABILITY OF FLUORO-CHLORO-HYDROCARBON

[75] Inventors: Werner Rudolph; Guenter Fernschild, both of Hanover, Fed. Rep. of Germany

[73] Assignee: Kali-Chemie AG, Hanover, Fed. Rep. of Germany

[21] Appl. No.: 258,054

[22] Filed: Apr. 28, 1981

[30] Foreign Application Priority Data

May 8, 1980 [DE] Fed. Rep. of Germany ....... 3017531

[51] Int. Cl.³ .............................................. F01K 25/08
[52] U.S. Cl. .......................................... 60/671; 60/657
[58] Field of Search .................... 62/474; 60/651, 671, 60/646, 657

[56] References Cited

U.S. PATENT DOCUMENTS

| 1,466,072 | 8/1923 | Todd | 62/474 |
| 1,809,834 | 6/1931 | Davenport | 62/474 |
| 2,341,430 | 2/1944 | Elsey | 62/474 |
| 2,381,354 | 8/1945 | Larson | 62/474 |
| 2,600,435 | 6/1952 | Shapiro | 62/474 |
| 2,951,350 | 9/1960 | Etherington | 62/474 |

OTHER PUBLICATIONS

Mechanical Engineers' Handbook, edited by Lionel S. Marks, McGraw Hill Co., New York, 1941.

*Primary Examiner*—Allen M. Ostrager
*Attorney, Agent, or Firm*—Schwartz, Jeffery, Schwaab, Mack, Blumenthal & Koch

[57] ABSTRACT

In order to prevent corrosion damage and to improve the thermal stability of fluoro-chloro-hydrocarbons, in an installation containing such circulating media, a highly active adsorption filter containing an adsorbing agent based on $Al_2O_3$ and/or $SiO_2$, and/or an adsorption filter containing a basic adsorbing agent is used. Also, iron-containing elements in contact with the working medium are passivated by hot nitriding.

17 Claims, 1 Drawing Figure

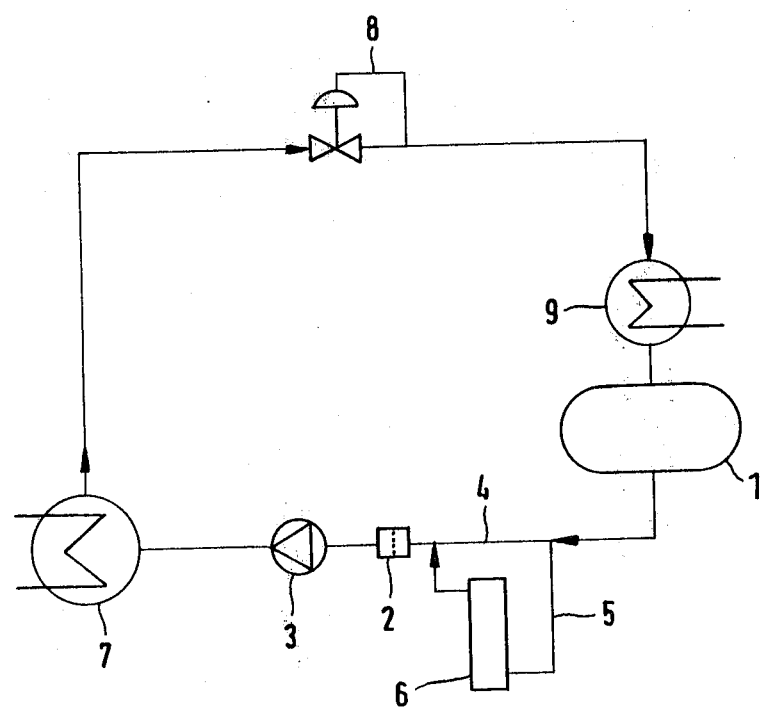

PROCESS FOR IMPROVING THE THERMAL STABILITY OF FLUORO-CHLORO-HYDROCARBON

BACKGROUND OF THE INVENTION

The present invention relates to an improved method for carrying out a Rankine cycle, and more especially to such a method for recovering waste heat by using a fluoro-chloro-hydrocarbon working medium.

Efforts to exploit new sources of energy are directed, inter alia, to the recovery and utilization of existing waste energies through the use of advanced technologies. Frequently, however, the energy involved is in the form of low temperature heat within the range, for example, of 20° C. to 300° C., which is still unused and is being discharged in large amounts into the environment. These waste heat fluxes include the waste gases of industrial conversion processes and streams of cooling water. Conversion of such low grade waste heats into electric energy has not been economically feasible heretofore, with the known technologies.

In conventional thermal power stations, the conversion of heat to electricity using water as the working medium takes place with the water in the liquid form and as steam. The use of water for this purpose is, however, advantageous only when the available heat is at a temperature above approximately 250° C. At temperatures between, for example, 80° and 250° C. water (steam) is not a suitable working medium, because, by virtue of its high specific volume it leads to relatively large and expensive apparatus and machinery.

Theoretical considerations and calculations generally lead to the recognition that, in particular, organic liquids with boiling temperatures significantly lower than that of water and with low specific volumes are especially suitable for this field of application, if, in addition to the above-mentioned requirement, they satisfy the following criteria:

They are non-combustible, non-toxic, thermally stable, chemically inert and low in cost.

Numerous fluoro-chloro-hydrocarbons satisfying most of the above-mentioned requirements are suitable as working and circulating media. Designers will select from the available number of fluoro-chloro-hydrocarbons those offering the best characteristics for the temperature range envisioned, such as, for example, $CFCl_3$ (R11), $CF_2Cl_2$ (R12), $CHF_2Cl$ (R22), $CF_2Cl—CFCl_2$ (R113), $CF_2Cl—CF_2Cl$ (R114), $CF_3—CF_2Cl$ (R115) or the like. These fluoro-chloro-hydrocarbons have demonstrated their suitability for technical use as cooling media in refrigerating assemblies for a long period of time and in large volumes.

As with other working media, for example, water, the use of fluoro-chloro-hydrocarbons as the working medium in Rankine processes (expansion processes) with respect to the yield in energy becomes more favorable with a rising difference in temperature between the evaporation and the condensation temperature. However, the fluoro-chloro-hydrocarbons which are preferably used, i.e., R 11, R 12, R 22, R 113, R 114 and R 115, tend to more or less strongly decompose with rising temperature within a temperature range of 80°–250° C. in the presence of steel and/or steel alloys, such as those used in the construction of power stations.

The following data is found in this context, in the Matheson Gas Data Book:

rate of decomposition of R 11 at 200° C. in steel: 2%/year
rate of decomposition of R 113 at 200° C. in steel: 6%/year In "Technical Bulletin B2" (1957)—Freon$^R$ (DuPont), in Table 1—Thermal Stability of Freon$^R$ Compounds—the following limiting temperatures of thermal stability are given:

| Compound | Maximum Temperature at Constant Exposure in the Presence of Oil/Steel and Copper (°C.) |
|---|---|
| R 11 | 107 |
| R 113 | 107 |
| R 12 | 121 |
| R 114 | 121 |
| R 22 | 135–149 |
| R 13 | 149 |

These data refer generally to "static" experiments, i.e., the fluoro-chloro-hydrocarbon and the metal specimen are exposed in a closed vessel to different test temperatures.

The material used is of decisive importance for the thermal stability of fluoro-chloro-hydrocarons. In the Matheson Gas Data Book, for the compounds R 11, R 12, R 22, R 113, and R 114, at elevated temperatures the following order of metal, in descending order of decomposition, is given: (max. decomposition) silver>brass>bronze>aluminum>1340 steel>copper>nickel>18-8 steel>Inconel$^R$ (min. decomposition).

For the technical application of fluoro-chloro-hydrocarbons in Rankine processes, this signifies that extended and problem-free operation in thermal power stations may be achieved only if either the working temperatures in such systems—when a carbon steel is used (for example St 39)—are kept very low, which would extensively restrict the economy of such an installation, or expensive steel alloys and/or special materials, for example, nickel, are employed. In this case again, the economy is strictly limited as a result of the high investment cost.

It is of decisive importance that such "waste heat recovery installations" be able to operate for long periods of time without failures and as free of maintenance as possible. This is achievable only if the thermolysis of the fluoro-chloro-hydrocarbon working medium is prevented or if the thermolysis products are removed from circulation. The term "thermolysis" is intended to signify that the working medium is thermally decomposed at elevated temperatures, whereby firstly the acid dissociation products of chloride and fluoride (in the form of hydrogen chloride and hydrogen fluoride, and possibly also chlorine and fluorine) are formed, and secondly, numerous organic halide by-products are generated.

The hydrolysis of fluoro-chloro-hydrocarbons caused by the residual water content in the working medium, which leads to HCl and HF in highly thermally stressed fluoro-chloro-hydrocarbon circulation systems, is particularly critical for the process. These hydrogen halide acids cause substantial corrosion. Furthermore, these iron-halogen compounds, such as, for example, $FeF_3$ and $FeCl_3$ may act as catalysts for isomerization and disproportionation reactions with the fluoro-chloro-hydrocarbons, potentially leading to a change in the thermodynamic and chemical behavior of the fluoro-chloro-hydrocarbon employed.

SUMMARY OF THE INVENTION

It is therefore an object of the present invention to provide an improved process for improving the thermal stability of fluoro-chloro-hydrocarbons.

It is also an object of the invention to provide a process for preventing corrosion damage in a system wherein a fluoro-chloro-hydrocarbon is exposed to an elevated temperature.

Another object of the invention resides in the provision of an improved thermal power installation, particularly of the type using a fluoro-chloro-hydrocarbon as the working medium.

Still another object of the invention is to provide an improved apparatus for carrying out a Rankine cycle process utilizing a fluoro-chloro-hydrocarbon as the working medium.

Finally, it is a further object of the invention to provide an improved process for recovering waste heat which is available at a temperature of between about 20° C. and 300° C.

In accomplishing the foregoing and other objects, there has been provided in accordance with the present invention a process for improving the thermal stability of fluoro-chloro-hydrocarbons and/or for preventing corrosion damage in a system wherein a fluoro-chloro-hydrocarbon is exposed to elevated temperatures, comprising the steps of circulating a fluoro-chloro-hydrocarbon around a system wherein the fluoro-chloro-hydrocarbon is exposed to a temperature which is sufficiently high to cause decomposition of the fluoro-chloro-hydrocarbon; and selectively passing the fluoro-chloro-hydrocarbon over an adsorption filter containing an adsorption medium selected from a high activity adsorption medium comprising non-basic $Al_2O_3$, a high activity adsorption medium comprising $SiO_2$, a basic adsorption medium, or a combination thereof. All of the fluoro-chloro-hydrocarbon may be passed over the filter, or the fluoro-chloro-hydrocarbon may be circulated in a divided stream and only one part of the divided stream passed over the filter. The fluoro-chloro-hydrocarbon may be passed continuously over the filter or it may be passed discontinuously over the filter.

In a preferred embodiment, the process further comprises the step of passivating by hot nitriding at least some and preferably all of the highly thermal stressed equipment parts in contact with said fluoro-chloro-hydrocarbon, for example, by contacting the equipment parts with a mixture of ammonia and nitrogen at a temperature in excess of about 500° C.

In accordance with another aspect of the present invention, there has been provided an apparatus for carrying out a Rankine process, utilizing a fluoro-chloro-hydrocarbon working medium, comprising a condenser; an evaporator; a fluid conduit path connecting the condenser and the evaporator; and an adsorption filter located in the conduit path between the condenser and said evaporator. Preferably, the apparatus further comprises a layer of passivating nitride on the surface of at least one and more preferably all of the iron-containing elements which are thermally stressed and are in contact with the working medium.

Further objects, features and advantages of the present invention will become apparent from the detailed description of preferred embodiments which follows, when considered together with the attached figure of drawing.

BRIEF DESCRIPTION OF THE DRAWING

The FIGURE of drawing is a schematic illustration of an installation for carrying out a Rankine cycle process according to the present invention.

DETAILED DESCRIPTION OF PREFERRED EMBODIMENTS

Surprisingly and unexpectedly, a process has been found which significantly improves the thermal stability of fluoro-chloro-hydrocarbons in Rankine cycle processes and/or prevents corrosion damage in apparatus which contains a fluoro-chloro-hydrocarbon as the circulating medium and is exposed to high temperatures. The process is characterized in that the fluoro-chloro-hydrocarbon is passed over a highly active adsorption filter, containing an adsorption medium based on $Al_2O_3$ and/or $SiO_2$ and/or is passed over an adsorption filter containing a basic adsorption medium.

The different measures are explained as follows:

1. Complete removal of water from the working medium. Under the thermal conditions of the cycle process, particularly in the part exposed to high temperatures of the thermal power station, even very slight amounts of 2 to 10 ppm $H_2O$ in the fluoro-chloro-hydrocarbon lead to the hydrolysis of the fluoro-chloro-hydrocarbon, with formation of the acid compounds HCl and HF. It is therefore absolutely necessary to remove even the slightest traces of moisture from the system, whereby preferably $H_2O$ contents of less than 1 ppm are maintained in the cycling medium. It is known to treat fluorocarbons with desiccant beads and molecular sieves, in order to reduce the $H_2O$ content to the values of 2 to 10 ppm. Generally, values lower than these cannot be achieved without a substantial technical effort. It has been discovered, surprisingly, that highly active adsorption media based on $Al_2O_3$ and/or $SiO_2$ make possible the removal of $H_2O$ in industrial installations to a value of 1 ppm. As the highly active adsorption agent based on $Al_2O_3$, molecular sieves and, in particular, highly active $Al_2O_3$ are suitable, with $Al_2O_3$ for column chromatography (for example, products of the WOELM CO.) being preferred. The invention thus relates to a process for the nearly absolute drying of the working medium, characterized in that a highly active adsorption agent is inserted in the working medium cycle, preferably in the condensed phase, so that the working medium may flow directly or in a bypass through the adsorption medium. In the operation of such a thermal engine, it is optional to operate the $H_2O$ adsorption continuously or in intervals. The size and the number of the adsorbers is also optional.

In general, 1 g of the highly active adsorption agent is sufficient for each 2 liters of the fluoro-chloro-hydrocarbon. This drying process has been found to be particularly advantageous during the filling and start-up of an installation. The known methods of drying such an installation by evacuation are time consuming and are not absolutely safe in complex industrial systems. It is possible, for example, for an amount of water sufficient for hydrolysis to remain, for example, in parts of a line behind valves, which must be kept closed during the evacuation. This water may enter the working medium in the instant the valve is opened. This dangerous disadvantage is eliminated by circulating the working medium over the highly active adsorption filter in a thermal power installation prior to the start-up. In the intervals between such filtering, the potentially exhausted filter may be replaced by a fresh absorber. A similar working method is conceivable also during an eventual refilling of the installation with fresh fluoro-chlorohydrocarbon. In this manner, it is assured that all of the parts in contact with the working medium are free of water. However, the application of this method does not exclude the possibility of using very dry fluoro-chloro-hydrocarbons with residual water contents of less than 1 ppm, after the installation has been flushed with fluoro-chloro-hydrocarbons, whereby the $H_2O$ content of the working medium is further reduced to a significant degree.

A further, supplemental effect of the adsorption filter is the result of the fact that fine particles of rust and dirt are filtered out by the adsorbing layer. In particular, iron oxides are converted rapidly by HCl and HF into iron halides, which in turn, when dissolved in the working medium, are removed by the absorber.

2. Removal of the chloride and fluoride acid components.

In a continuously operated thermal engine or heat pump, the possibility of a slight thermolysis of fluoro-chloro-hydrocarbon due to a temporary over-heating of short duration, for example, in the flue gas, cannot be excluded. In order to prevent the appearance of corrosion phenomena in the system, it is necessary to remove from the working medium fluoride and chloride acid components which are responsible for the corrosion. It has now been discovered that this important function may be effected advantageously with a basic adsorption medium. Basic oxides, in particular the oxides of the alkaline earth metals or zinc, are suitable as the basic adsorption agents. In another variant, basic aluminum oxide, particularly basic $Al_2O_3$ used for column chromatography, may be employed. By means of the adsorption arrangement according to the invention, a neutral pH value in the circulating medium may be maintained over long periods of time in thermal power installations.

This neutralization effect may be increased substantially if the basic adsorption agent is added to the highly active adsorption medium in the form of a mixed bed. Care must be taken, however, that the water formed in a reaction of, for example, calcium oxide with, for example, HF and HCl is adsorbed with certainty on a subsequent layer of highly active aluminum oxide.

In this arrangement, dehydration may also be obtained by highly active adsorption agents based on $SiO_2$, without the formation of Si halide compounds.

Each of the individual features of the invention produces by itself a substantial improvement of the thermal stability of fluoro-chloro-hydrocarbon materials, in particular the compounds R 11, R12, R 22, R 113, R 114 and R 115.

An additional safety feature may be provided by the passivation of all thermally stressed, iron-containing parts of the apparatus in contact with the fluoro-chloro-hydrocarbon, by means of a hot nitriding procedure. The nitriding of steel or steel alloys is effected with (gaseous) ammonia at temperatures in excess of about 500° C., preferably from about 500° to 800° C. Through the formation of iron nitride on the surface of the metal, a passivating effect with respect to the fluoro-chloro-hydrocarbons is attained. It is important that the surface passivation is effected by means of a thermal nitriding process. This assures that at the prevailing working temperatures the surface of the nitrided steel will not be destroyed by the thermal expansion of the material, thereby providing points of origin for corrosion.

In this manner, the decomposition temperature in the case of R 11 as the working medium in carbon steel (St 39) can be raised from 170° C. to 210° C. by nitriding the parts and lines conducting hot gas, and by nitriding alloy steel (St 4571) it can be raised from 210° C. to 220° C. This shows that grades of steel with lower iron contents also experience improvements concerning the thermal stability behavior of fluoro-chloro-hydrocarbons as the result of nitriding. Inexpensive carbon steels, such as those used in this field of equipment building, are raised to the level of alloy steels. However, this measure in itself is not sufficient to assure working continuously at temperatures in excess of 200° C.

By the complete removal of water from fluoro-chloro-hydrocarbons with high activity (basic) $Al_2O_3$ intended for column chromatography, the decomposition temperature in the case of R 11 may be raised from 170° C. to 250° C. in an untreated carbon steel, without a change being observed over extended periods of time in the working medium.

The removal of the acid compounds HF and HCl from the circulating medium R 11, which is exposed for a short period of time to an evaporator temperature of 290° C., is effected completely by the use of highly active basic $Al_2O_3$ for column chromatography. The R 11 reacted neutral. This eliminated the replacement of the working medium, which in industrial applications amounts to an appreciable savings in cost.

By means of a combination of the individual features according to the invention, the decomposition temperature for R 11 in carbon steel (St 39) was raised from 170° C. to 270° C. in an experimental installation, wherein actual operating conditions were simulated in relation to pressure and temperature and the variation of pressure and temperature.

The process of the invention to improve the thermal stability behavior of fluoro-chloro-hydrocarbons makes it possible now to use the waste heat offered in numerous locations at 80° to 300° for the generation of electric power or as a mechanical driving force, wherein water is no longer suitable as the working medium in a Rankine process. Applications are not restricted to the generation of electric power and mechanical driving energy. It is also possible to construct heat pumps which, beyond the present state of the art, are capable of producing, for example, water or steam at a temperature greater than 150° C.

The process of the invention shall be described in more detail by the examples presented hereinafter.

(a) EXPERIMENTAL APPARATUS

The investigation of the process according to the invention for the improvement of the thermal stability behavior of fluoro-chloro-hydrocarbons, in particular, the types R 11, R 12, R 22, R 113, R 114 and R 115, was carried out in a dynamic experimental installation, wherein actual operating conditions were silumated in relation to temperature and pressure, the variation of temperature and pressure, and the use of different structural materials, oils and seals.

The experimental apparatus is constructed in the manner of a compact installation, wherein the cycling process takes place as follows, with reference to the figure of drawing.

The circulating medium is taken from the condensate collector 1 and passed through a mechanical filter 2 to the feed pump 3. The adsorption filter 6 with the high activity aluminum oxide packing (basic) for column chromatography, (product of the WOELM CO.) is located in a bypass line 5. By means of this arrangement, it is possible to conduct the circulating medium to the feed pump 3 either directly or through the adsorption filter. The feed pump transports the heat carrier medium—in keeping with the predetermined pressure and flow volume—into the evaporator 7. This evaporator coil is located in an electrically heated oil bath. The evaporated working medium is then transported to a pneumatic control valve 8, which simulates the function of a turbine or a vapor engine. After expansion, the working medium passes into the condenser 9, which comprises a water cooled coil, and is condensed therein and collected in the condensate collector vessel 1.

The circulating volume of the working medium amounted to 36 kg/h. Prior to each experimental series, the entire installation was carefully cleaned.

(b) NITRIDING

The nitriding of the evaporator tube and of all of the lines and valves carrying hot vapors was effected in the following manner.

The parts made of a carbon steel or Grade 4571 steel were initially thoroughly cleaned and degreased. After drying, the parts were exposed in a furnace at temperatures rising from 600° to 750° C. to a flow of ammonia and nitrogen (the latter as the inert gas) in a volume ratio of 2:1 and a flow rate of 15 l/h. Test tubes were inserted to control the degree of nitriding.

After 8 hours, the iron on the surface of the metal had been converted to γ-iron nitride (X-ray fine structure analysis). Subsequently, all of the parts were inserted into the test apparatus.

The working medium was controlled by means (1) analytical determination of the fluoride and the chloride content and (2) by gas chromatography.

The analytical samples were taken downstream of the evaporator, in front of the feed pump and downstream of the Al$_2$O$_3$ adsorber.

(c) EXAMPLES

Example 1

In the experimental apparatus described hereinabove (not nitrided), initially the effect of the different structural materials on the thermal decomposition of R 11 and R 113 was investigated as a function of temperature. The circulation of the working medium amounted to 36 kg/h. The pressure was adapted in keeping with the vapor pressure curve minus 10%—to exclude condensation—of the individual evaporator temperature. In Table 1 the fluoride and chloride content in the flow of hot gas is given as a function of temperature, together with the gas chromatographic analyses. The experimental time for each temperature setting was 180 operating hours.

TABLE 1

| Temperature of the hot gas after the evaporator °C. | CARBON STEEL St 39 Content ppm | | GC F-% | | ALLOY STEEL St 4571 Content ppm | | GC F-% | | ALLOY STEEL St 4309 Content ppm | | GC F-% | |
|---|---|---|---|---|---|---|---|---|---|---|---|---|
| R 11 | F' | Cl' | R 11 | Residue | F' | Cl' | R 11 | Residue | F' | Cl' | R 11 | Residue |
| 20 | 0.1 | 0.1 | 99.99 | 0.01 | 0.1 | 4.0 | 99.98 | 0.02 | 0.1 | 3.1 | 99.98 | 0.02 |
| 150 | 0.1 | 0.5 | 99.99 | 0.01 | | | | | 0.7 | 2.1 | 99.98 | 0.02 |
| 170 | 0.1 | 0.5 | 99.99 | 0.01 | 0.1 | 2.9 | 99.98 | 0.02 | 0.1 | 0.2 | 99.98 | 0.02 |
| 180 | 0.1 | 0.5 | 99.99 | 0.01 | 0.1 | 0.8 | 99.98 | 0.02 | 0.1 | 0.1 | 99.97 | 0.03 |
| 190 | 1.0 | 2.8 | 99.98 | 0.02 | 0.1 | 0.7 | 99.98 | 0.02 | 0.1 | 0.2 | 99.96 | 0.04 |
| 200 | 1.4 | 12.9 | 99.97 | 0.02 | 0.1 | 0.7 | 99.98 | 0.03 | 0.2 | 0.6 | 99.96 | 0.04 |
| 210 | 1.7 | 4.5 | 99.97 | 0.03 | 0.1 | 0.5 | 99.97 | 0.03 | 0.2 | 0.6 | 99.96 | 0.04 |
| 220 | | | | | 0.3 | 1.8 | 99.98 | 0.02 | 0.1 | 0.5 | 99.96 | 0.04 |
| 230 | | | | | 3.0 | 17.7 | 99.97 | 0.02 | 0.9 | 4.5 | 99.96 | 0.04 |
| 240 | | | | | 16.0 | 207.0 | 99.95 | 0.05 | 1.4 | 11.2 | 99.70 | 0.30 |
| 250 | | | | | | | | | | | | |
| R 113 | F' | Cl' | R 113 | Residue | F' | Cl' | R 113 | Residue | F' | Cl' | R 113 | Residue |
| 20 | 0.1 | 0.2 | 99.98 | 0.02 | 0.1 | 0.3 | 99.98 | 0.02 | 0.1 | 0.3 | 99.98 | 0.02 |
| 120 | 0.1 | 0.2 | 99.98 | 0.02 | 0.1 | 0.7 | 99.98 | 0.02 | | | | |
| 140 | | | | | | | | | | | | |
| 150 | 0.0 | 0.2 | 99.97 | 0.03 | 0.4 | 0.9 | 99.98 | 0.02 | | | | |
| 160 | 0.5 | 1.6 | 99.97 | 0.03 | 0.6 | 1.2 | 99.96 | 0.04 | 0.6 | 0.3 | 99.97 | 0.03 |
| 170 | 0.4 | 1.7 | 99.97 | 0.03 | 0.6 | 1.2 | 99.97 | 0.03 | 0.6 | 0.3 | 99.97 | 0.03 |
| 180 | 1.0 | 10.7 | 99.92 | 0.08 | 0.7 | 1.5 | 99.97 | 0.03 | 0.1 | 0.9 | 99.97 | 0.03 |
| 190 | 3.0 | 17.0 | 99.84 | 0.16 | 0.9 | 1.8 | 99.96 | 0.04 | 0.9 | 2.4 | 99.97 | 0.03 |
| 200 | | | | | 4.0 | 15.1 | 99.98 | 0.11 | 2.0 | 7.0 | 99.93 | 0.07 |
| 210 | | | | | | | | | | | | |
| 220 | | | | | | | | | | | | |
| 230 | | | | | | | | | | | | |

EXAMPLE 2

In the above-described experimental apparatus, the effect of nitrided carbon steel and Grade 4571 steel (prepared as under (b)) on the thermal decomposition of R 11 and R 113, was investigated. Experimental conditions corresponded to those of Example 1.

TABLE 2

| Temperature of the hot gas after the evaporator C.° | Nitrided Carbon Steel St 39 Content ppm | | GC F-% | | Nitrided Alloy Steel St 4571 Content ppm | | GC F-% | |
|---|---|---|---|---|---|---|---|---|
| | F' | Cl' | R 11 | Residue | F' | Cl' | R 11 | Residue |
| 20 | 0.1 | 2.6 | 99.97 | 0.03 | 0.1 | 2 | 99.98 | 0.02 |
| 170 | 0.1 | 0.7 | 99.96 | 0.06 | | | | |

TABLE 2-continued

| Temperature of the hot gas after the evaporator C.° | Nitrided Carbon Steel St 39 | | | | Nitrided Alloy Steel St 4571 | | | |
|---|---|---|---|---|---|---|---|---|
| | Content ppm | | GC F-% | | Content ppm | | GC F-% | |
| | F' | Cl' | R 113 | Residue | F' | Cl' | R 113 | Residue |
| 180 | 0.1 | 0.3 | 99.96 | 0.06 | 0.1 | 0.1 | 99.98 | 0.02 |
| 190 | 0.1 | 0.7 | 99.96 | 0.06 | 0.7 | 2.8 | 99.98 | 0.02 |
| 200 | 0.1 | 0.5 | 99.96 | 0.06 | 0.1 | 1.4 | 99.96 | 0.04 |
| 210 | 0.1 | 0.6 | 99.96 | 0.06 | 0.2 | 2.1 | 99.96 | 0.04 |
| 220 | 0.5 | 1.5 | 99.96 | 0.06 | 0.1 | 0.8 | 99.96 | 0.04 |
| 230 | 2.6 | 11.6 | 99.95 | 0.05 | 0.5 | 2.3 | 99.96 | 0.04 |
| 240 | | | | | 5.8 | 14.7 | 99.91 | 0.01 |
| 20 | 0.1 | 0.4 | 99.98 | 0.02 | | | | |
| 170 | 0.4 | 0.2 | 99.98 | 0.02 | | | | |
| 190 | 0.2 | 3.1 | 99.97 | 0.03 | | | | |
| 200 | 0.5 | 1.7 | 99.98 | 0.02 | | | | |
| 210 | 0.8 | 2.7 | 99.96 | 0.04 | | | | |
| 220 | 1.1 | 4.8 | 99.96 | 0.04 | | | | |
| 230 | 4.3 | 16.1 | 99.92 | 0.08 | | | | |

EXAMPLE 3

In the above-described experimental apparatus (not nitrided), a standard steel (St 39) was used as the line carrying the hot gas. The working medium R 11 was conducted selectively from the condensate collector directly to the feed pump or in the bypass over an aluminum oxide adsorber. A glass vessel with a volume of 300 ml served as the adsorber. Therein, 200 g of basic aluminum oxide of the WOELM CO. were placed. The working medium was charged on top onto the $Al_2O_3$ bed and removed at the bottom of the adsorber. It passed through a fine filter and arrived from there at the feed pump. After charging the installation, initially the working medium was pumped for 75 hours at 20° C. through the adsorber in order to obtain the complete drying of the working medium and of the equipment parts in contact with the working medium. Subsequently, the adsorber cartridge was replaced by a fresh cartridge and the system brought to operating temperature. The installation was operated so that, prior to each temperature setting, the working medium was passed for 2 hours over the adsorber. In Table 3, the contents in the acid components F' and Cl' and the variation of the gas composition as a function of temperature, are given.

EXAMPLE 4

In the above-described experimental apparatus, nitrided standard steel (St 39) was used in the evaparator coil and the line carrying hot gas. The experiment was conducted with R 11 as the working medium in accordance with Example 3, with the adsorber installed. The circulation of R 11 prior to the temperature program was reduced from 75 hours to 16 hours.

In Table 4 the onset of the decomposition of the working medium is demonstrated numerically.

TABLE 3

| Temperature of the hot gas after the evaporator °C. | R 11 | | | | R 113 | | | |
|---|---|---|---|---|---|---|---|---|
| | Content ppm | | GC F-% | | Content ppm | | GC F-% | |
| | Fl | Cl' | R 11 | Residue | F' | Cl' | R 113 | Residue |
| 20 | 0.7 | 1.0 | 99.98 | 0.02 | 0.3 | 0.6 | 99.98 | 0.02 |
| 170 | 0.9 | 9.4 | 99.98 | 0.02 | 0.1 | 1.2 | 99.98 | 0.02 |
| 180 | 0.1 | 1.3 | 99.98 | 0.02 | 0.1 | 0.9 | 99.98 | 0.02 |
| 190 | 0.1 | 1.5 | 99.97 | 0.03 | 0.1 | 0.3 | 99.98 | 0.02 |
| 200 | 0.1 | 0.3 | 99.98 | 0.02 | 0.1 | 0.3 | 99.98 | 0.02 |
| 210 | 0.1 | 0.1 | 99.98 | 0.02 | 0.1 | 0.1 | 99.96 | 0.04 |
| 220 | 0.1 | 0.1 | 99.98 | 0.02 | 0.1 | 0.2 | 99.97 | 0.03 |
| 230 | 0.1 | 0.1 | 99.97 | 0.03 | 0.2 | 1.0 | 99.95 | 0.05 |
| 240 | 0.2 | 0.1 | 99.96 | 0.04 | 1.1 | 3.4 | 99.78 | 0.22 |
| 250 | 0.5 | 0.6 | 99.96 | 0.04 | | | | |
| 260 | 1.9 | 17.5 | 99.82 | 0.08 | | | | |
| 270 | 3.1 | 61.6 | 99.88 | 0.12 | | | | |
| 280 | | | | | | | | |
| 290 | | | | | | | | |

TABLE 4

| Temperature of the hot gas after the evaporator °C. | Working Medium R 11 | | | |
|---|---|---|---|---|
| | Content ppm | | | GC Residue |
| | F' | Cl' | R 11 | |
| 20 | 0.1 | 0.2 | 99.98 | 0.02 |
| 180 | 0.3 | 0.7 | 99.98 | 0.02 |
| 200 | 0.1 | 0.6 | 99.98 | 0.02 |
| 210 | 0.1 | 0.1 | 99.96 | 0.04 |
| 220 | 0.1 | 0.2 | 99.97 | 0.03 |
| 230 | 0.1 | 0.1 | 99.97 | 0.03 |
| 240 | 0.1 | 0.1 | 99.97 | 0.03 |
| 250 | 0.1 | 0.6 | 99 96 | 0.03 |
| 260 | 0.2 | 0.6 | 99.96 | 0.04 |
| 270 | 1.2 | 4.8 | 99.93 | 0.07 |

EXAMPLE 5

In the above-described experimental apparatus, during an experiment carried out in keeping with Example 3, the adsorption was investigated of basic, high activity $Al_2O_3$ for column chromatography, with respect to the acid components HF and HCl. During a circulation phase, wherein the circulating medium passed through the adsorption filter, samples were taken both before and after the adsorber and their acidity determined. In Table 5, the fluoride and chloride contents before and after the adsorption are given.

TABLE 5

| Adsorption Period (h) | Fluoride and Chloride Content | | | |
|---|---|---|---|---|
| | Before Adsorption (ppm) | | After Adsorption (ppm) | |
| | F' | Cl' | F' | Cl' |
| 0 | 6.8 | 26.4 | <0.1 | <0.3 |
| 1 | 0.4 | 2.1 | <0.1 | <0.3 |
| 2 | 0.6 | 0.5 | <0.1 | <0.3 |
| 3 | 0.2 | <0.3 | <0.1 | <0.3 |
| 4 | 0.1 | <0.3 | <0.1 | <0.3 |

EXAMPLE 6

In the above-described experimental apparatus (not nitrided), during an experiment according to Example 3, the adsorption behavior of an adsorber consisting of high activity $Al_2O_3$ for column chromatography and different alkaline earth oxides was investigated with respect to the acid components HF and HCl. The adsorption filter consisted of 190 g $Al_2O_3$ and 10 g magnesium oxide, the latter being placed in the inlet part of the adsorber.

TABLE 6

| Adsorption Period (h) | Fluoride and Chloride Content | | | |
|---|---|---|---|---|
| | Before Adsorption (ppm) | | After Adsorption (ppm) | |
| | F' | Cl' | F' | Cl' |
| 0 | 6.8 | 26.4 | <0.1 | <0.3 |
| 1 | 0.2 | 1.2 | <0.1 | <0.3 |
| 2 | <0.1 | <0.3 | <0.1 | <0.3 |
| 3 | <0.1 | <0.3 | <0.1 | <0.3 |

The adsorption capacity is increased with an adsorber composition of 190 g $Al_2O_3$ and 10 g of an alkaline earth oxide or ZnO as follows:

| | |
|---|---|
| $Al_2O_3$ + — | 100.0% |
| $Al_2O_3$ + MgO | 100.0% |
| $Al_2O_3$ + BaO | 118% |
| $Al_2O_3$ + CaO | 102% |
| $Al_2O_3$ + ZnO | 108% |

What is claimed is:

1. A process for improving the thermal stability of fluoro-chloro-hydrocarbons and for preventing corrosion damage in a system wherein a fluoro-chloro-hydrocarbon is exposed to elevated temperatures, comprising the steps of:
   circulating a fluoro-chloro-hydrocarbon around a system wherein the fluoro-chloro-hydrocarbon is exposed to a temperature between about 80° C. and 300° C. which is sufficiently high to cause decomposition of the fluoro-chloro-hydrocarbon; and
   selectively passing the fluoro-chloro-hydrocarbon over an adsorption filter containing an adsorption medium consisting essentially of a basic high activity $Al_2O_3$.

2. A process according to claim 1, wherein said fluoro-chloro-hydrocarbon comprises an aliphatic fluoro-chloro-hydrocarbon.

3. A process according to claim 1, wherein said adsorption filter contains a highly active $Al_2O_3$ for column chromatography.

4. A process according to claim 1, wherein the fluoro-chloro-hydrocarbon is passed over the adsorption medium in the condensed form.

5. A process according to claim 1, wherein the fluoro-chloro-hydrocarbon is circulated in a divided stream and only one part of the divided stream is passed over the filter.

6. A process according to claim 1, wherein the fluoro-chloro-hydrocarbon is passed continuously over the filter.

7. A process according to claim 1, wherein the fluoro-chloro-hydrocarbon is passed discontinuously over the filter.

8. A process according to claim 1, wherein said system comprises highly thermal stressed equipment parts and said system has been passivated by hot nitriding at least some of the highly thermal stressed equipment parts in contact with said fluoro-chloro-hydrocarbon.

9. A process according to claim 8, wherein the hot nitriding comprises contacting the equipment parts with a mixture of ammonia and nitrogen.

10. A process according to claim 8, wherein said hot nitriding is effected at a temperature in excess of about 500° C.

11. A process according to claim 10, wherein said hot nitriding is effected at a temperature of between about 500° and 800° C.

12. A process according to claim 1, wherein the fluoro-chloro-hydrocarbon is passed over said adsorption filter for a period of time sufficient to lower the water content of the hydrocarbon down to about 1 ppm.

13. A process according to claim 1, wherein the adsorption filter contains a single-component adsorption medium consisting essentially of a basic high activity $Al_2O_3$.

14. An apparatus for carrying out a Rankine process, utilizing a fluoro-chloro-hydrocarbon working medium, comprising:
   a condenser;
   an evaporator;
   a fluid conduit path connecting said condenser and said evaporator;
   means for operating said evaporator at a temperature between about 80° C. and 300° C.; and
   an adsorption filter located in said conduit path between said condenser and said evaporator, said filter containing an adsorption medium consisting essentially of a basic high activity $Al_2O_3$.

15. An apparatus according to claim 14, further comprising a layer of passivating nitride on the surface of at least one iron-containing element which is thermally stressed and is in contact with the working medium.

16. A process for recovering waste heat, comprising the steps of:
   conducting a Rankine cycle utilizing a fluoro-chloro-hydrocarbon as the working medium therein and using the waste heat, which is available at a temperature between about 80° C. and 300° C., as a heat source; and
   improving the thermal stability of the fluoro-chloro-hydrocarbon working medium by selectively passing the fluoro-chloro-hydrocarbon over an adsorption filter containing an adsorption medium consisting essentially of a basic high activity $Al_2O_3$.

17. A process according to claim 16, wherein the fluoro-chloro-hydrocarbon is passed over said adsorption filter for a period of time sufficient to lower the water content of the hydrocarbon down to about 1 ppm.

* * * * *